United States Patent
Kundu et al.

(10) Patent No.: US 10,335,031 B1
(45) Date of Patent: Jul. 2, 2019

(54) VITALS MONITORING SYSTEM

(71) Applicant: Accenture Global Solutions Limited, Dublin (IE)

(72) Inventors: Abir Kundu, Kolkata (IN); Joydeep Bhaduri, Kolkata (IN); Biswarup Roy, Kolkata (IN); Zubair Hussain, Srinagar (IN); Ramya Kumar, Pune (IN)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 15/950,785

(22) Filed: Apr. 11, 2018

(51) Int. Cl.
| G08B 21/00 | (2006.01) |
| A61B 5/00 | (2006.01) |
| G16H 80/00 | (2018.01) |
| A61B 5/0205 | (2006.01) |
| A61B 5/145 | (2006.01) |
| A61B 5/024 | (2006.01) |

(52) U.S. Cl.
CPC ............ *A61B 5/0022* (2013.01); *A61B 5/746* (2013.01); *G16H 80/00* (2018.01); *A61B 5/0006* (2013.01); *A61B 5/0008* (2013.01); *A61B 5/0205* (2013.01); *A61B 5/02438* (2013.01); *A61B 5/145* (2013.01); *A61B 5/6801* (2013.01)

(58) Field of Classification Search
CPC ..... A61B 5/0022; A61B 5/746; A61B 5/6801; A61B 5/02438; A61B 5/0006; A61B 5/145; A61B 5/0008; A61B 5/0205; G16H 80/00

USPC ............................................. 340/573.1, 540
See application file for complete search history.

(56) References Cited

U.S. PATENT DOCUMENTS

| 8,292,807 | B2* | 10/2012 | Perkins | ................ | A61B 5/0002 600/301 |
| 2008/0281168 | A1* | 11/2008 | Gibson | ................ | A61B 5/0205 600/301 |
| 2013/0045685 | A1* | 2/2013 | Kiani | ..................... | G08B 21/24 455/41.2 |
| 2013/0317753 | A1* | 11/2013 | Kamen | ............... | G06F 19/3418 702/19 |
| 2015/0164438 | A1* | 6/2015 | Halperin | ................ | A61B 5/746 340/573.1 |
| 2016/0051206 | A1* | 2/2016 | De Waele | .............. | A61B 5/746 600/301 |

\* cited by examiner

*Primary Examiner* — Anh V La
(74) *Attorney, Agent, or Firm* — Harrity & Harrity, LLP

(57) ABSTRACT

A remote care system may include a platform that includes one or more memory devices and one or more processors communicatively coupled to the one or more memory devices. The platform may connect and communicate bi-directionally with a plurality of devices via a gateway device. At least some of the plurality of devices may include sensors capable of gathering vitals data from a patient. The vitals data may include different types of vitals data. The platform may connect and communicate bi-directionally with another plurality of devices. The other plurality of devices may be remote to the gateway device and the at least some of the plurality of devices. The platform may support continuous and live streaming of the vitals data from the sensors. The platform may perform a set of actions on a per patient basis based on analyzing the vitals data.

20 Claims, 6 Drawing Sheets

VITALS MONITORING SYSTEM

BACKGROUND

A care provider may perform actions to maintain or improve the health of a patient via prevention, diagnosis, and treatment of disease, illness, injury, and/or other physical or mental impairments in the patient. Care may include primary care, secondary care, and tertiary care, as well as public health.

SUMMARY

According to some possible implementations, a system may include a platform that includes one or more memory devices and one or more processors communicatively coupled to the one or more memory devices. The platform may connect and communicate bi-directionally with a plurality of devices via a gateway device. The plurality of devices may include different types of devices and devices manufactured by a plurality of different third parties. At least some of the plurality of devices may include sensors capable of gathering vitals data from a patient. The vitals data may include a plurality of different types of vitals data. The platform may support continuous and live streaming of the vitals data from the sensors. The platform may receive threshold data on a per patient basis. The threshold data may identify a baseline for one or more of the plurality of different types of vitals data. The platform may selectively generate an alert based on the vitals data and the threshold data. The platform may provide the alert to a responsible party when the alert is generated.

According to some possible implementations, a patient monitoring system may include a platform that includes one or more memory devices and one or more processors communicatively coupled to the one or more memory devices. The platform may connect and communicate bi-directionally with a plurality of devices via a gateway device. At least some of the plurality of devices may be wearable devices that include sensors capable of gathering vitals data from a patient. The at least some of the plurality of devices may be located in a same location as the gateway device. The platform may support continuous and live streaming of the vitals data from the sensors. The platform may perform an analysis of the vitals data on a per patient basis. The platform may selectively generate an alert based on a result of performing the analysis. The platform may provide the alert to a responsible party when the alert is generated.

According to some possible implementations, a remote care system may include a platform that includes one or more memory devices and one or more processors communicatively coupled to the one or more memory devices. The platform may connect and communicate bi-directionally with a plurality of devices via a gateway device. At least some of the plurality of devices may include sensors capable of gathering vitals data from a patient. The vitals data may include a plurality of different types of vitals data. The platform may connect and communicate bi-directionally with another plurality of devices. The other plurality of devices may be remote to the gateway device and the at least some of the plurality of devices. The platform may support continuous and live streaming of the vitals data from the sensors. The platform may perform a set of actions on a per patient basis based on analyzing the vitals data.

DETAILED DESCRIPTION

The following detailed description of example implementations refers to the accompanying drawings. The same reference numbers in different drawings may identify the same or similar elements.

To provide healthcare to a patient, a provider (e.g., a doctor, a nurse, and/or the like) typically needs to be physically present to perform check-ups on the patient, to communicate healthcare strategies to the patient, and/or the like. For example, the patient may need to travel to a doctor's office, may need to be checked-in to a hospital, and/or the like to receive healthcare from a provider. This system of providing healthcare to a patient is inefficient, as healthcare provisioning is confined by a physical location. In addition, providing healthcare in this manner reduces a quantity of patients that a provider can serve (e.g., due to the provider having to move from patient room to patient room, having to gather current vitals data prior to consulting with the patient, and/or the like).

Some implementations described herein provide a system that is capable of utilizing sensors, remote and local client devices, and a vitals monitoring platform to gather and analyze vitals data related to a patient. In this way, the system provides a tool that facilitates remote provisioning of healthcare to a patient by a provider, in a manner not previously possible. This reduces or eliminates physical constraints on providing healthcare to a patient, thereby improving an efficiency of providing healthcare to the patient. In addition, this reduces an amount of time needed to provide healthcare to a patient, thereby improving a quantity of patients to which a provider can provide healthcare and/or reducing an amount of time that a patient needs to wait to receive healthcare. Further, by providing a system that can gather and/or analyze real-time vitals data for a patient, the system facilitates more accurate and real-time (or near real-time) adjustments to healthcare being provided to the patient, thereby improving provisioning of healthcare to the patient.

Figure 1:
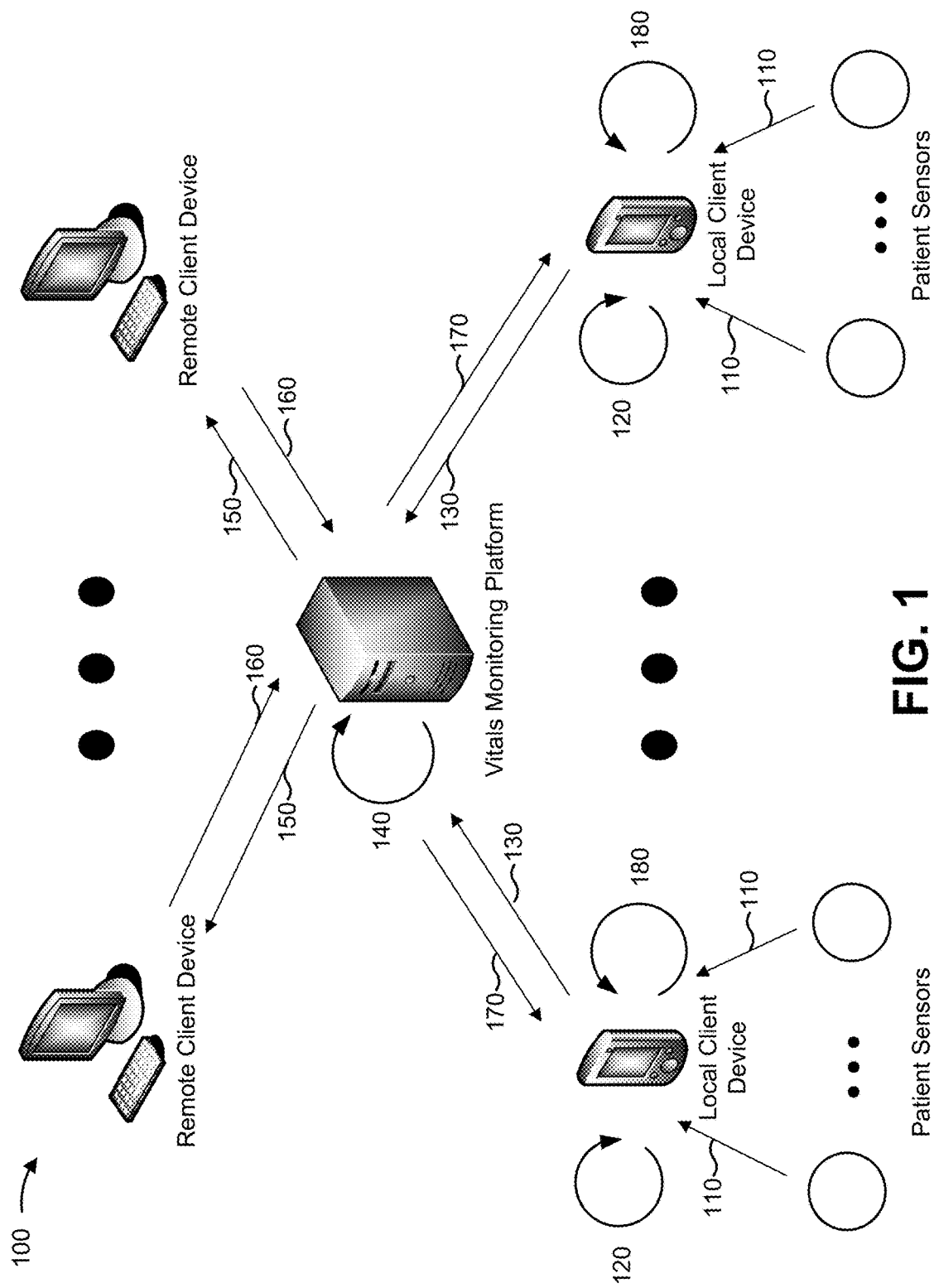
FIG. 1 is a diagram of an overview of an example implementation described herein.

FIG. 1 is a diagram of an overview of an example implementation 100 described herein. As shown in FIG. 1, implementation 100 includes various sets of patient sensors, a set of local client devices (e.g., where a local client device is associated with a respective set of patient sensors), a vitals monitoring platform, and a set of remote client devices.

In some implementations, these devices may comprise a patient monitoring system, a remote care system, and/or the like. In some implementations, a set of patient sensors may be included in one or more wearable devices worn by the patient and/or otherwise configured to gather vitals data from the patient, as described elsewhere herein. In some implementations, a set of patient sensors may be wirelessly connected to a local client device, which may be in a same location as the set of sensors and/or the patient (e.g., in a same room as the set of sensors or the patient, in a same building as the set of sensors and/or the patient, and/or the like). For example, a local client device may be a bed-side device in a hospital room. In some implementations, the set of local client devices may be connected to the vitals monitoring platform via a network, such the Internet (e.g., the vitals monitoring platform may be cloud based, may be located in a data center off site from the local client devices, and/or the like). In this way, the set of local client devices may function as a set of gateway devices between various sets of patient sensors and the vitals monitoring platform.

In some implementations, the vitals monitoring platform may be connected to the set of remote client devices via a network. In some implementations, the set of remote client devices may be located at a location that is different than the set of patient sensors, the set of local client devices, and/or the patient. For example, a patient may be located in a hospital and a remote client device may be located at an office of a doctor, or the patient may be located at the home of the patient and the remote client device may be located at a hospital or a doctor's office of a doctor providing healthcare to the patient.

As shown in FIG. 1, and by reference numbers 110, the sets of patient sensors may provide, to respective local client devices, vitals data gathered from respective patients. For example, a set of patient sensors may gather heart rate data, blood pressure data, body temperature data, respiratory rate data, oxygen saturation data, electrocardiography data, and/or the like from the patient and may provide this data to a corresponding local client device via a wireless connection between the set of patient sensors and the local client device (e.g., via a Wi-Fi connection, a Bluetooth connection, a Bluetooth Low Energy (BLE) connection, and/or the like) based on the respective local client device being within communicative proximity of the set of patient sensors. In this way, a local client device may receive different types of vitals data from different types of patient sensors (e.g., a heart rate monitor that gathers heart rate data, a thermometer device that gathers temperature data, and/or the like).

In some implementations, a set of patient sensors may encrypt the vitals data prior to sending the vitals data to a local client device (e.g., using a hash function, an advanced encryption standard (AES) algorithm, public-private key encryption, and/or the like) and/or may provide the vitals data via a secure wireless connection (e.g., a hypertext transfer protocol secure (HTTPS) connection, a secure shell (SSH) tunnel, and/or the like) to secure the vitals data. In some implementations, the set of patient sensors may provide the vitals data at an interval, according to a schedule, based on receiving a request for the vitals data from a local client device, when values included in the vitals data satisfies a threshold, in a streaming (e.g., continuous) manner as the vitals data is collected, and/or the like.

As shown by reference numbers 120, the set of local client devices may process the vitals data and/or perform one or more other actions related to the vitals data and/or a respective set of patient sensors. For example, a local client device may determine whether values included in the vitals data satisfy a threshold (e.g., as an initial screening step before providing the vitals data to the vitals monitoring platform). This conserves processing resources and/or network resources that would otherwise be consumed providing the vitals data to the vitals monitoring platform when the vitals data does not satisfy a threshold.

Additionally, or alternatively, and as another example, a local client device may monitor a battery level of a battery of a respective set of patient sensors and may trigger an alarm, may output sensory output (e.g., a sound, light, etc.), and/or the like to indicate to a nurse that a battery level of a battery satisfies a threshold. Similarly, a local client device may send a message to another client device (e.g., a remote client device via the vitals monitoring platform) to notify a health care provider that a battery level of a patient sensor satisfies a threshold, that a value for vitals data satisfies a threshold, and/or the like. Additionally, or alternatively, and as another example, a local client device may format the vitals data so that the vitals data is in a format that the vitals monitoring platform can use (e.g., after determining that a value for the vitals data satisfies a threshold), thereby conserving processing resources of the vitals monitoring platform that would otherwise be consumed formatting the data, conserving processing resources of the vitals monitoring platform that would otherwise be consumed via slower processing of unformatted data, and/or the like.

As shown by reference numbers 130, the set of local client devices may provide the vitals data to the vitals monitoring platform. For example, the set of local client devices may provide vitals data in a manner that is the same as or similar to the manner in which the sets of patient sensors provided the vitals data. Continuing with the previous example, the set of local client devices may wait until a threshold amount of vitals data is received before sending the vitals data, may provide the vitals data in a streaming manner, may provide the vitals data after encrypting the vitals data, may provide the vitals data via a secure connection, and/or the like.

In some implementations, different local client devices may provide the vitals data according to different schedules, based on receiving different requests for the vitals data, at different intervals, and/or the like. For example, the vitals monitoring platform may manage data related to monitoring of vitals data for hundreds, thousands, or more patients (e.g., may manage a frequency at which vitals data is to be collected, a type of vitals data to be collected, and/or the like). Continuing with the previous example, the vitals monitoring platform may configure the set of local client devices to provide vitals data based on a respective patient with which the vitals data is associated, may request the vitals data from the set of local client devices according to different schedules, and/or the like. In this way, the vitals monitoring platform can manage collection of vitals data in a manner not possible by a human actor.

As shown by reference number 140, the vitals monitoring platform may process the vitals data and/or may perform one or more actions related to the vitals data. For example, the vitals monitoring platform may analyze the vitals data to determine whether values included in the vitals data satisfy a threshold (e.g., on a per patient basis), may use a machine learning model to determine whether combinations of values in the vitals data indicate a potential issue with the health of a patient, and/or the like, may determine a score for the health of a patient and/or for a specific condition being monitored (e.g., using a machine learning model), and/or the like, as described elsewhere herein. In some implementations, the vitals monitoring platform may process vitals data for hundreds, thousands, or more patients in real-time (or near real-time). In this way, the vitals monitoring platform may process vitals data in a manner not possible by a human actor.

Additionally, or alternatively, and as another example, the vitals monitoring platform may send a message to a client device associated with a healthcare provider (e.g., a remote client device) based on processing the vitals data. For example, the vitals monitoring platform may send a message to a remote client device associated with a doctor, a nurse, and/or the like associated with a patient when the vitals data includes values that satisfy a threshold, when a score related to the patient satisfies a threshold, and/or the like. In some implementations, the vitals monitoring platform may dynamically monitor results of processing vitals data for hundreds, thousands, or more patients and may dynamically send notifications based on the results, in a manner not possible by a human actor. Additionally, or alternatively, the vitals monitoring platform may schedule a meeting between a healthcare provider associated with a remote client device and another healthcare provider or a patient associated with a local client device based on a result of processing vitals data. For example, the vitals monitoring platform may use electronic calendars associated with individuals to attend the meeting to identify an available time for the meeting and may generate a calendar item on the electronic calendars for the meeting.

As shown by reference numbers 150, the vitals monitoring platform may provide vitals data to the set of remote client devices. For example, the vitals monitoring platform may provide the vitals data in a continuous and live streaming manner, in real-time (or near real-time) as the vitals data is gathered by the sets of patient sensors and/or is provided to the vitals monitoring platform, and/or the like. In some implementations, the vitals monitoring platform may provide the vitals data for display via a user interface and may update the user interface in a continuous and live manner as the vitals data is received from the set of local client devices. For example, the user interface may include graphs, charts, gauges, and/or the like for displaying the vitals data (e.g., current values for the vitals data, values for the vitals data over time, and/or the like). In some implementations, the vitals monitoring platform may trigger an alarm via the set of remote client devices based on a result of processing and/or analyzing the vitals data, may send a message for display via a display associated with the remote client device, and/or the like.

As shown by reference numbers 160, the set of remote client devices may provide a set of instructions to the vitals monitoring platform. For example, the set of instructions may cause the vitals monitoring platform to generate a set of graphical outputs based on the vitals data (e.g., charts, graphs, etc. that show the vitals data over time, in relation to historical values, in relation to population averages, etc.). Additionally, or alternatively, and as another example, the set of instructions may be related to modifying operations of a patient sensor (e.g., may be related to causing the patient sensor to increase a rate of monitoring the vitals data, to causing the patient sensor to decrease the rate of monitoring vitals data, to causing the patient sensor to initiate an idle state, to causing the patient sensor to terminate an idle state, etc.). Additionally, or alternatively, and as another example, the set of instructions may relate to causing the vitals monitoring platform to establish an audio conferencing or a video conferencing session with a particular local client device.

As shown by reference numbers 170, the vitals monitoring platform may provide the set of instructions to the appropriate local client device and/or may perform another action based on receiving the set of instructions. For example, the vitals monitoring platform may provide a set of instructions to a local client device to modify operations of a respective set of patient sensors. Additionally, or alternatively, and as another example, the vitals monitoring platform may establish an audio conferencing session or a video conferencing session between a remote client device and a local client device (e.g., by establishing a peer-to-peer (P2P) communication between the remote client device and the local client device using a web real-time communication (WebRTC) protocol). In some implementations, the vitals monitoring platform may manage hundreds, thousands, or more sets of instructions and/or sets of actions related to hundreds, thousands, or more local client devices.

As shown by reference numbers 180, the set of local client devices may perform respective actions based on receiving the set of instructions from the vitals monitoring platform and/or based on another action performed by the vitals monitoring platform. For example, a local client device may modify operations of a patient sensor. Additionally, or alternatively, and as another example, a local client device may provide, to a remote client device, communications associated with an audio conferencing session and/or a video conferencing session, such as audio data, video data, and/or the like.

In this way, the vitals monitoring platform may connect to and facilitate bi-directional communications among devices (e.g., remote client devices, local client device, and/or patient sensors) related to providing healthcare services to a patient. This facilitates provisioning of remote healthcare services to the patient, thereby improving a capability of a provider to provide the healthcare services. In addition, this reduces or eliminates a need for a set of devices to be dedicated to a patient (e.g., a provider can use a single remote client device to monitor and/or provide healthcare services to multiple patients), thereby reducing a quantity of devices needed to provide healthcare services to multiple patients. Further, this facilitates centralized management of patents on an individualized basis, thereby improving an accuracy of providing care to multiple patients (e.g., by facilitating analysis of healthcare being provided to a patient in relation to the history of the patient, healthcare being provided to other patients, etc.), facilitating population-based analytics to provide faster detection of health-related issues, and/or the like.

In addition, in this way, several different stages of the process for gathering and/or processing vitals data are automated, which may remove human subjectivity and waste from the process, and which may improve speed and efficiency of the process and conserve computing resources (e.g., processor resources, memory resources, and/or the like). Furthermore, implementations described herein use a rigorous, computerized process to perform tasks or roles that were not previously performed or were previously performed using subjective human intuition or input. For example, currently there does not exist a technique to manage gathering and/or processing of vitals data. Furthermore, automating the process for gathering, processing, and/or managing vitals data conserves computing resources (e.g., processor resources, memory resources, and/or the like) that would otherwise be wasted in attempting to gather unneeded vitals data.

As indicated above, FIG. 1 is provided merely as an example. Other examples are possible and may differ from what was described with regard to FIG. 1. Although FIG. 1 was described in the context of providing healthcare to a patient, the implementations are not limited to this context and could apply to other contexts, such as monitoring vitals data for an operator of a vehicle, for an individual working around toxic chemicals, and/or the like.

Figure 2:
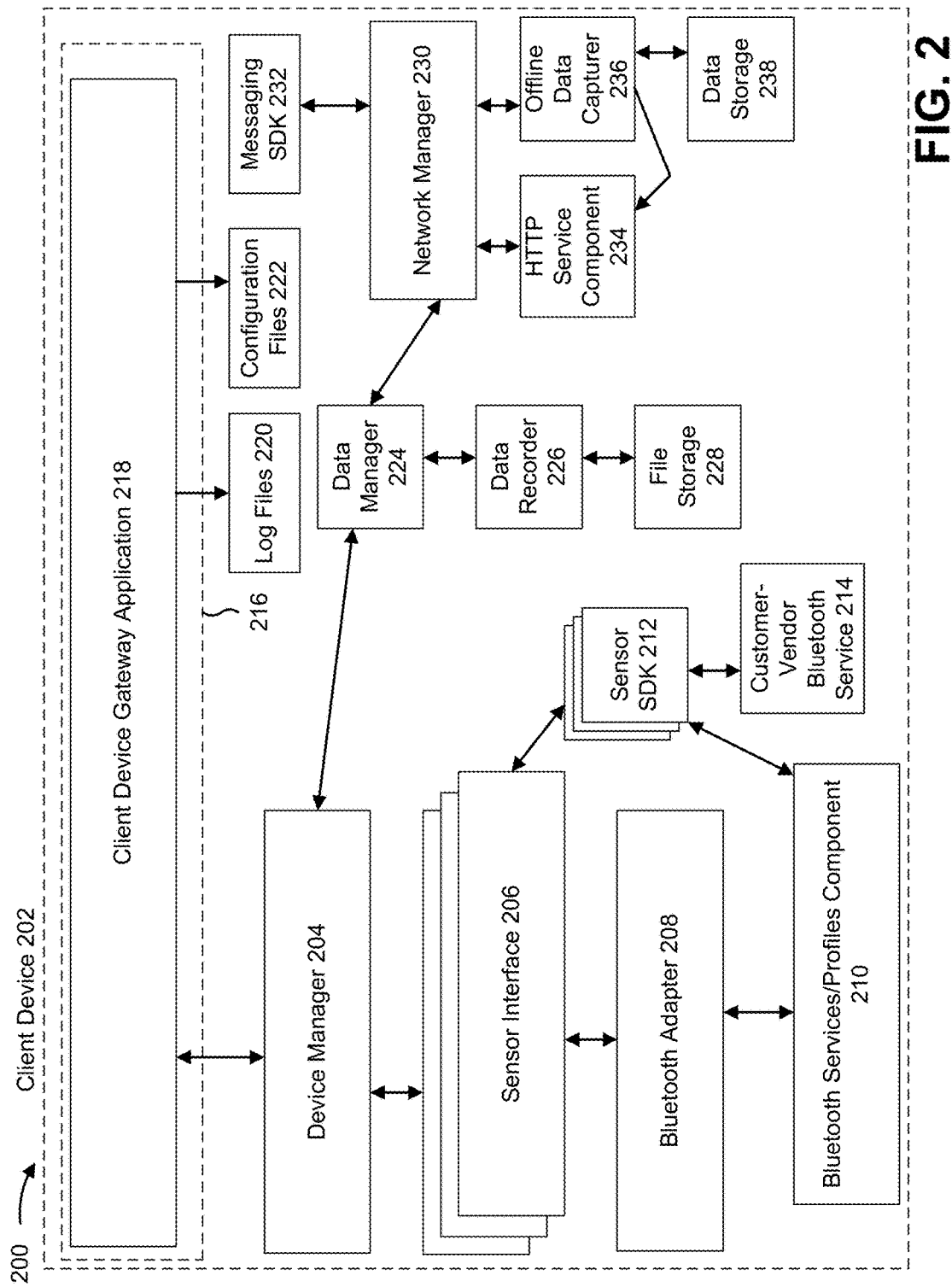
FIG. 2 is a diagram of an example implementation described herein.

FIG. 2 is a diagram of an example implementation 200 described herein. FIG. 2 shows example components of a client device, such as a local client device described with regard to FIG. 1, and the interaction of the various components of this device.

As shown in FIG. 2, implementation 200 includes a client device 202 similar to other client devices described elsewhere herein. In some implementations, client device 202 may include a device manager 204. For example, device manager 204 may include a common interface to facilitate communications with a set of sensor devices. In some implementations, client device 202 may include a set of sensor interfaces 206. For example, the sensor interfaces 206 may provide client device 202 with specific capabilities needed to communicate with respective sensors (e.g., may provide client device 202 with a capability to use a protocol associated with a sensor, to use particular commands associated with a sensor, etc.). In some implementations, device manager 204 and sensor interface 206 may communicate to discover a sensor, to start and/or pause data collection by a sensor, and/or the like. In some implementations, client device 202 may include a Bluetooth adapter 208. For example, Bluetooth adapter 208 may provide client device 202 with a capability to perform Bluetooth-related functions, such as initiating device discovery, querying a list of paired devices, creating a Bluetooth server socket to listen for connection requests, and/or the like. In some implementations, sensor interface 206 and Bluetooth adapter 208 may communicate so that communications (e.g., instructions, vitals data, etc.) can be exchanged between client device 202 and a sensor.

In some implementations, client device 202 may include a Bluetooth services/profiles component 210. For example, Bluetooth services/profiles component 210 may define the manner in which client device 202 uses Bluetooth technology (e.g., a manner in which multimedia data is streamed over a Bluetooth connection, a manner in which messages are exchanged among devices associated with a Bluetooth connection, and/or the like). In some implementations, client device 202 may include a sensor software development kit (SDK) 212. For example, sensor SDK 212 may provide compatibility between client device 202 and a vendor-specific operating system, protocol, and/or the like. In some implementations, client device 202 may include a customer-vendor Bluetooth service component 214. For example, customer-vendor Bluetooth service component 214 may define a vendor-specific manner in which client device 202 is to use Bluetooth technology.

In some implementations, client device 202 may include a front end 216. For example, front end 216 may include applications, user interfaces, and/or the like related to controlling client device 202. As a specific example, front end 216 may include a client device gateway application 218 that is associated with displaying vitals data and/or that communicates with device manager 204 to control data capture from a sensor (e.g., remote control of the sensor). In some implementations, device manager 204 and client device gateway application 218 may communicate via an application programming interface (API), such as to start and/or pause data collection by a sensor, to record data, and/or the like. Additionally, or alternatively, client device 202 may use client device gateway application 218 to communicate with a vitals monitoring platform.

In some implementations, client device 202 may include log files 220. For example, log files 220 may gather and/or store reports related to dropped connections between client device 202 and a sensor, application crashes (e.g., crashes of client device gateway application 218), and/or the like. In some implementations, client device 202 may include configuration files 222. For example, configuration files 222 may store user-specific configurations for client device gateway application 218 (e.g., an arrangement of a user interface, a manner in which vitals data is displayed, and/or the like), client device 202 configurations (e.g., a rate at which client device 202 is to receive and/or request vitals data from a sensor, a rate at which client device 202 is to provide the vitals data to a vitals monitoring platform, etc.), and/or the like.

In some implementations, client device 202 may include a data manager 224. For example, data manager 224 may receive and/or store vitals data from a sensor (e.g., in chronological order, by sensor, and/or the like). In some implementations, client device 202 may include a data recorder 226. For example, data recorder 226 may store data by writing the data to memory resources of client device 202, organizing the data into files, and/or the like. In some implementations, device manager 204 and data manager 224 may communicate via an API. In some implementations, client device 202 may include file storage 228. For example, file storage 228 may store data generated by client device 202, received by client device 202, and/or the like.

In some implementations, client device 202 may include a network manager 230. For example, network manager 230 may receive vitals data from data manager 224, may consolidate vitals data (e.g., by sensor, by time, etc.), may send vitals data to a vitals monitoring platform, may store vitals data (e.g., when client device 202 is not connected to the vitals monitoring platform), and/or the like. In some implementations, client device 202 may include a messaging SDK 232. For example, messaging SDK 232 may provide client device 202 with a capability to communicate with the vitals monitoring platform. In some implementations, client device 202 may include a hypertext transfer protocol (HTTP) service component 234. For example, HTTP service component 234 may facilitate transfer of vitals data to the vitals monitoring platform via an HTTP connection with the vitals monitoring platform. In some implementations, client device 202 may include an offline data capturer 236. For example, offline data capturer 236 may store vitals data (e.g., in data storage 238) by sensor, in a chronological order in which the vitals data was received, and/or the like when client device 202 is not connected to the vitals monitoring platform. In some implementations, when client device 202 uses offline data capturer 236 to store vitals data, the offline data capturer 236 may provide vitals data to HTTP service component 234 so that the vitals data can be provided to the vitals monitoring platform.

As indicated above, FIG. 2 is provided merely as an example. Other examples are possible and may differ from what was described with regard to FIG. 2. The number and arrangement of devices and/or components shown in FIG. 2 are provided as an example. In practice, implementation 200 may include additional devices and/or components, fewer devices and/or components, different devices and/or components, or differently arranged devices and/or components than those shown in FIG. 2. Additionally, or alternatively, a set of devices and/or components (e.g., one or more devices and/or components) of implementation 200 may perform one or more functions described as being performed by another set of devices and/or components of implementation 200.

Figure 3:
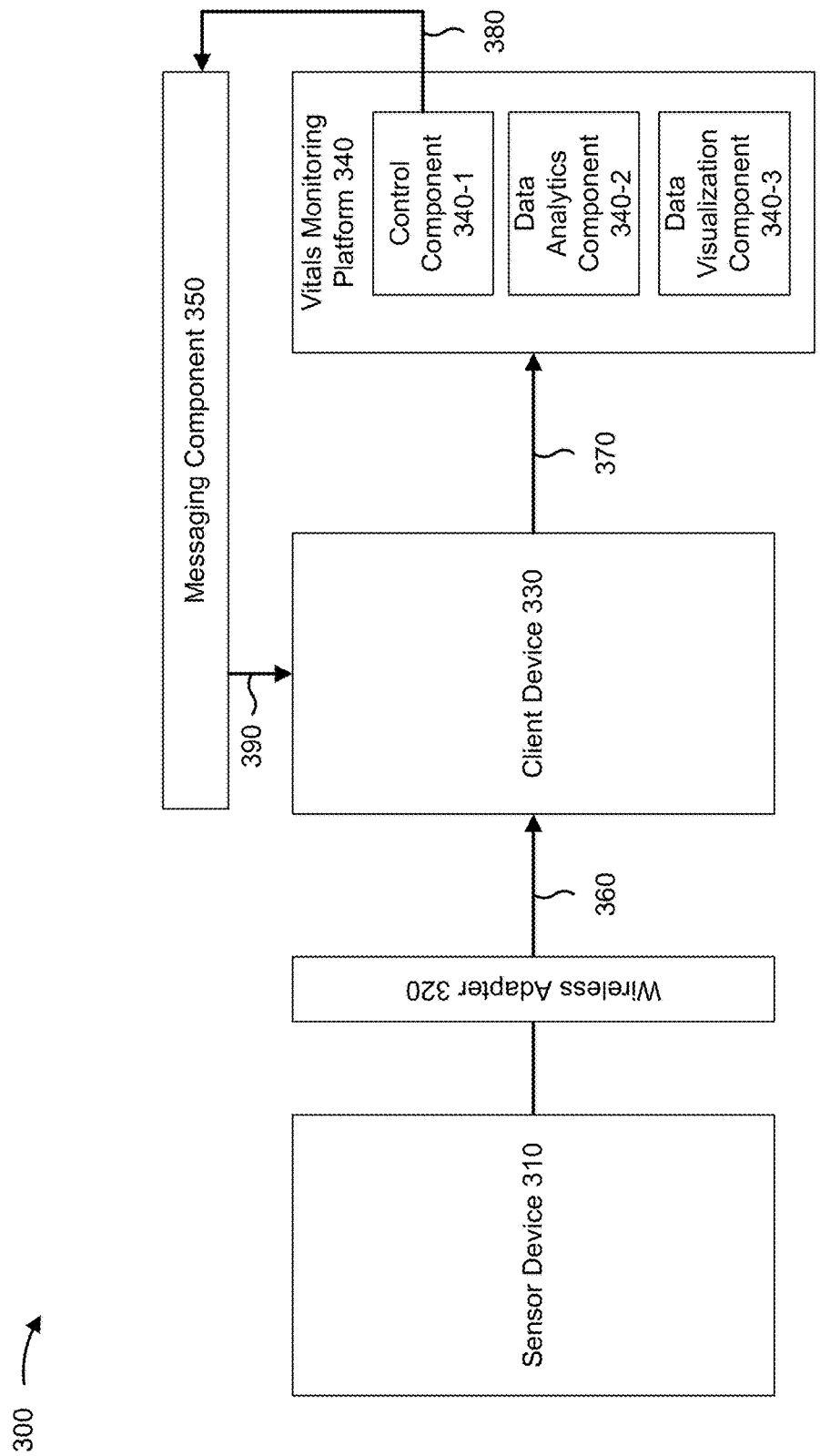
FIG. 3 is a diagram of an example implementation described herein.

FIG. 3 is a diagram of an example implementation 300 described herein. FIG. 3 shows interactions between devices and/or components related to gathering vitals data.

As shown in FIG. 3, implementation 300 may include a sensor device 310. For example, sensor device 310 may be the same as or similar to other sensors described elsewhere herein. As further shown, implementation 300 may include wireless adapter 320. For example, wireless adapter 320 may include a Bluetooth adapter, a Wi-Fi adapter, and/or the like, similar to that described elsewhere herein. As further shown in FIG. 3, implementation 300 may include a client device 330. For example, client device 330 may be the same as or similar to other client devices described elsewhere herein.

As further shown in FIG. 3, implementation 300 may include a vitals monitoring platform 340 (e.g., that includes control component 340-1, data analytics component 340-2, and/or data visualization component 340-3). For example, vitals monitoring platform 340 may be the same as or similar to other vitals monitoring platforms described elsewhere herein. In some implementations, control component 340-1 may be related to controlling operations of sensor device 310. For example, control component 340-1 may generate instructions related to controlling sensor device 310, may communicate the instructions to sensor device 310, and/or the like. In some implementations, data analytics component 340-2 may be related to analyzing vitals data (e.g., determining whether values included in the vitals data satisfy a threshold, detecting a trend and/or a pattern in the vitals data, using a model to detect particular combinations of values in the vitals data, and/or the like). In some implementations, data visualization component 340-3 may generate graphical output for the vitals data, for a result of analyzing the vitals data, and/or the like.

As shown by reference number 360, sensor device 310 may provide vitals data to client device 330 using wireless adapter 320 (e.g., via a Bluetooth connection, a Wi-Fi connection, and/or the like). As shown by reference number 370, client device 330 may provide vitals data to vitals monitoring platform 340 (e.g., via a network, such as the Internet). As shown by reference numbers 380 and 390, vitals monitoring platform 340 (e.g., using control component 340-1) may provide a set of instructions to client device 330 (e.g., via messaging component 350). For example, the set of instructions may be included in a firebase cloud messaging (FCM) notification.

As indicated above, FIG. 3 is provided merely as an example. Other examples are possible and may differ from what was described with regard to FIG. 3. The number and arrangement of devices and/or components shown in FIG. 3 are provided as an example. In practice, implementation 300 may include additional devices and/or components, fewer devices and/or components, different devices and/or components, or differently arranged devices and/or components than those shown in FIG. 3. Additionally, or alternatively, a set of devices and/or components (e.g., one or more devices and/or components) of implementation 300 may perform one or more functions described as being performed by another set of devices and/or components of implementation 300.

Figure 4:
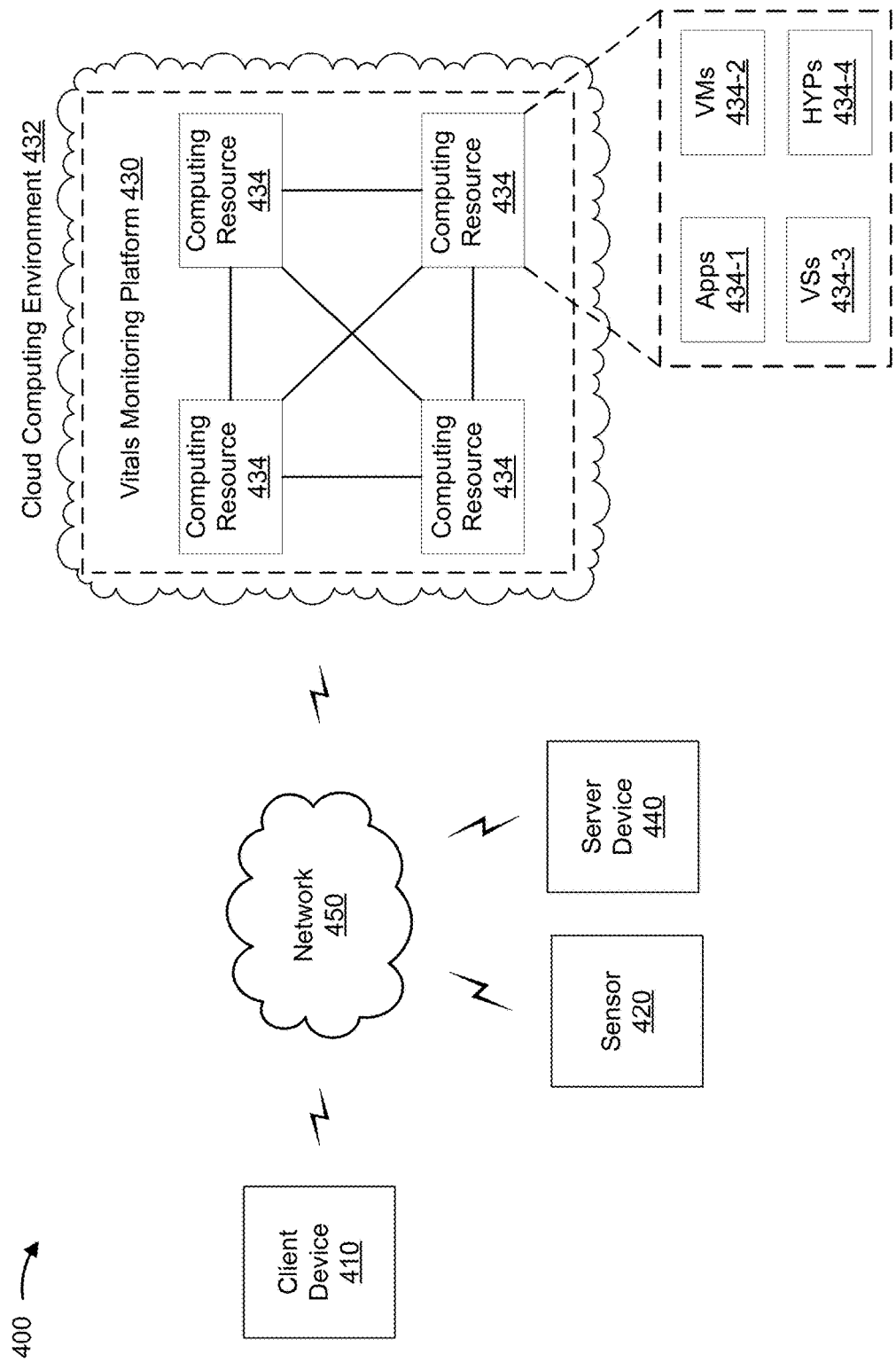
FIG. 4 is a diagram of an example environment in which systems and/or methods, described herein, may be implemented.

FIG. 4 is a diagram of an example environment 400 in which systems and/or methods, described herein, may be implemented. As shown in FIG. 4, environment 400 may include a client device 410, a sensor 420, a vitals monitoring platform 430 within a cloud computing environment 432 that includes a set of computing resources 434 (e.g., referred to collectively as "computing resources 434" and individually as "computing resource 434"), a server device 440, and a network 450. Devices of environment 400 may interconnect via wired connections, wireless connections, or a combination of wired and wireless connections.

Client device 410 includes one or more devices capable of receiving, generating, storing, processing, and/or providing vitals data related to a patient. For example, client device 410 may include a mobile phone (e.g., a smart phone, a radiotelephone, etc.), a laptop computer, a tablet computer, a handheld computer, a gaming device, a wearable communication device (e.g., a smart wristwatch, a pair of smart eyeglasses, etc.), a desktop computer, or a similar type of device. In some implementations, client device 410 may be located local to sensor 420, as described elsewhere herein. In some implementations, client device 410 may be located remote to sensor 420, as described elsewhere herein. Additionally, or alternatively, client device 410 may receive vitals data from sensor 420 and may provide the vitals data to vitals monitoring platform 430, as described elsewhere herein. In some implementations, client device 410 may function as a gateway device between sensor 420 and vitals monitoring platform 430 (e.g., may function as a communication intermediary between sensor 420 and vitals monitoring platform 430).

Sensor 420 includes one or more devices capable of receiving, generating, storing, processing, and/or providing vitals data from a patient (e.g., a human patient or an animal patient). For example, sensor 420 may include a blood pressure monitor, an oximeter, a glucometer, an airflow sensor, Galvanic skin response sensor, electrocardiogram sensor, a heart rate monitor, a scale, a pulse oximeter, a thermometer, or a similar type of device. In some implementations, sensor 420 may be implemented within a wearable device (e.g., a smart wristwatch, a pair of smart eyeglasses, an activity band, and/or the like), as described elsewhere herein. In some implementations, sensor 420 may provide vitals data to client device 410 after gathering the vitals data (e.g., a local client device 410), as described elsewhere herein. Additionally, or alternatively, sensor 420 may be controlled remotely by client device 410 via vitals monitoring platform 430, as described elsewhere herein.

In some implementations, a patient may be associated with multiple sensors 420 that are of different types and/or manufactured by different third parties. For example, a patient may be associated with a blood pressure monitor and a heart rate monitor, which are gathering vitals data from the patient and which may be manufactured by different third parties (e.g., may utilize different communication interfaces, different protocols, different messaging schemes, and/or the like). In this way, by gathering data from multiple different sensors 420, vitals monitoring platform 430 may be capable of managing a complex system of sensors 420. Although sensor 420 was described as gathering vitals data from a patient, sensor 420 may include a device that gathers environmental data of an environment in which the patient is located (e.g., humidity data, air temperature data, whether particular chemicals are present in the environment, and/or the like).

Vitals monitoring platform 430 includes one or more devices capable of receiving, generating, storing, processing, and/or providing vitals data related to a patient. For example, vitals monitoring platform 430 may include a cloud server or a group of cloud servers. In some implementations, vitals monitoring platform 430 may be designed to be modular such that certain software components can be swapped in or out depending on a particular need. As such, vitals monitoring platform 430 may be easily and/or quickly reconfigured for different uses.

In some implementations, as shown, vitals monitoring platform 430 may be hosted in cloud computing environment 432. Notably, while implementations described herein describe vitals monitoring platform 430 as being hosted in cloud computing environment 432, in some implementations, vitals monitoring platform 430 may not be cloud-based (i.e., may be implemented outside of a cloud computing environment) or may be partially cloud-based.

Cloud computing environment 432 includes an environment that hosts vitals monitoring platform 430. Cloud computing environment 432 may provide computation, software, data access, storage, and/or other services that do not require end-user knowledge of a physical location and configuration of a system and/or a device that hosts vitals monitoring platform 430. As shown, cloud computing environment 432 may include a group of computing resources 434 (referred to collectively as "computing resources 434" and individually as "computing resource 434").

Computing resource 434 includes one or more personal computers, workstation computers, server devices, or another type of computation and/or communication device. In some implementations, computing resource 434 may host vitals monitoring platform 430. The cloud resources may include compute instances executing in computing resource 434, storage devices provided in computing resource 434, data transfer devices provided by computing resource 434, etc. In some implementations, computing resource 434 may communicate with other computing resources 434 via wired connections, wireless connections, or a combination of wired and wireless connections.

As further shown in FIG. 4, computing resource 434 may include a group of cloud resources, such as one or more applications ("APPs") 434-1, one or more virtual machines ("VMs") 434-2, one or more virtualized storages ("VSs") 434-3, or one or more hypervisors ("HYPs") 434-4.

Application 434-1 includes one or more software applications that may be provided to or accessed by one or more devices of environment 400. Application 434-1 may eliminate a need to install and execute the software applications on devices of environment 400. For example, application 434-1 may include software associated with vitals monitoring platform 430 and/or any other software capable of being provided via cloud computing environment 432. In some implementations, one application 434-1 may send/receive information to/from one or more other applications 434-1, via virtual machine 434-2. In some implementations, application 434-1 may include a software application associated with one or more databases and/or operating systems. For example, application 434-1 may include an enterprise application, a functional application, an analytics application, and/or the like.

Virtual machine 434-2 includes a software implementation of a machine (e.g., a computer) that executes programs like a physical machine. Virtual machine 434-2 may be either a system virtual machine or a process virtual machine, depending upon use and degree of correspondence to any real machine by virtual machine 434-2. A system virtual machine may provide a complete system platform that supports execution of a complete operating system ("OS"). A process virtual machine may execute a single program, and may support a single process. In some implementations, virtual machine 434-2 may execute on behalf of a user (e.g., a user of client device 410), and may manage infrastructure of cloud computing environment 432, such as data management, synchronization, or long-duration data transfers.

Virtualized storage 434-3 includes one or more storage systems and/or one or more devices that use virtualization techniques within the storage systems or devices of computing resource 434. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 434-4 provides hardware virtualization techniques that allow multiple operating systems (e.g., "guest operating systems") to execute concurrently on a host computer, such as computing resource 434. Hypervisor 434-4 may present a virtual operating platform to the guest operating systems, and may manage the execution of the guest operating systems. Multiple instances of a variety of operating systems may share virtualized hardware resources.

Server device 440 includes one or more devices capable of receiving, generating storing, processing, and/or providing vitals data associated with a patient. For example, server device 440 may include a server (e.g., in a data center or a cloud computing environment), a data center (e.g., a multi-server micro datacenter), a workstation computer, a virtual machine (VM) provided in a cloud computing environment, or a similar type of device. In some implementations, server device 440 may include a communication interface that allows server device 440 to receive information from and/or transmit information to other devices in environment 400. In some implementations, server device 440 may be a physical device implemented within a housing, such as a chassis. In some implementations, server device 440 may be a virtual device implemented by one or more computer devices of a cloud computing environment or a data center. In some implementations, server device 440 may provide, to vitals monitoring platform 430, vitals data, data related to a threshold, and/or the like, as described elsewhere herein.

Network 450 includes one or more wired and/or wireless networks. For example, network 450 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

Although FIG. 4 shows a single client device 410, a single sensor 420, and a single server device 440, in reality, environment 400 may include multiple client devices 410, multiple sensors 420, and/or multiple server devices 440. For example, multiple client devices 410 may be associated with respective sets of sensors 420 and respective patients (e.g., hundreds, thousands, or more client devices 410, sets of sensors 420, and/or patients). In this way, vitals monitoring platform 430 may be connected to a complex set of client devices 410 and/or sensors 420.

The number and arrangement of devices and networks shown in FIG. 4 are provided as an example. In practice, there may be additional devices and/or networks, fewer devices and/or networks, different devices and/or networks, or differently arranged devices and/or networks than those shown in FIG. 4. Furthermore, two or more devices shown in FIG. 4 may be implemented within a single device, or a single device shown in FIG. 4 may be implemented as multiple, distributed devices. Additionally, or alternatively, a set of devices (e.g., one or more devices) of environment 400 may perform one or more functions described as being performed by another set of devices of environment 400.

Figure 5:
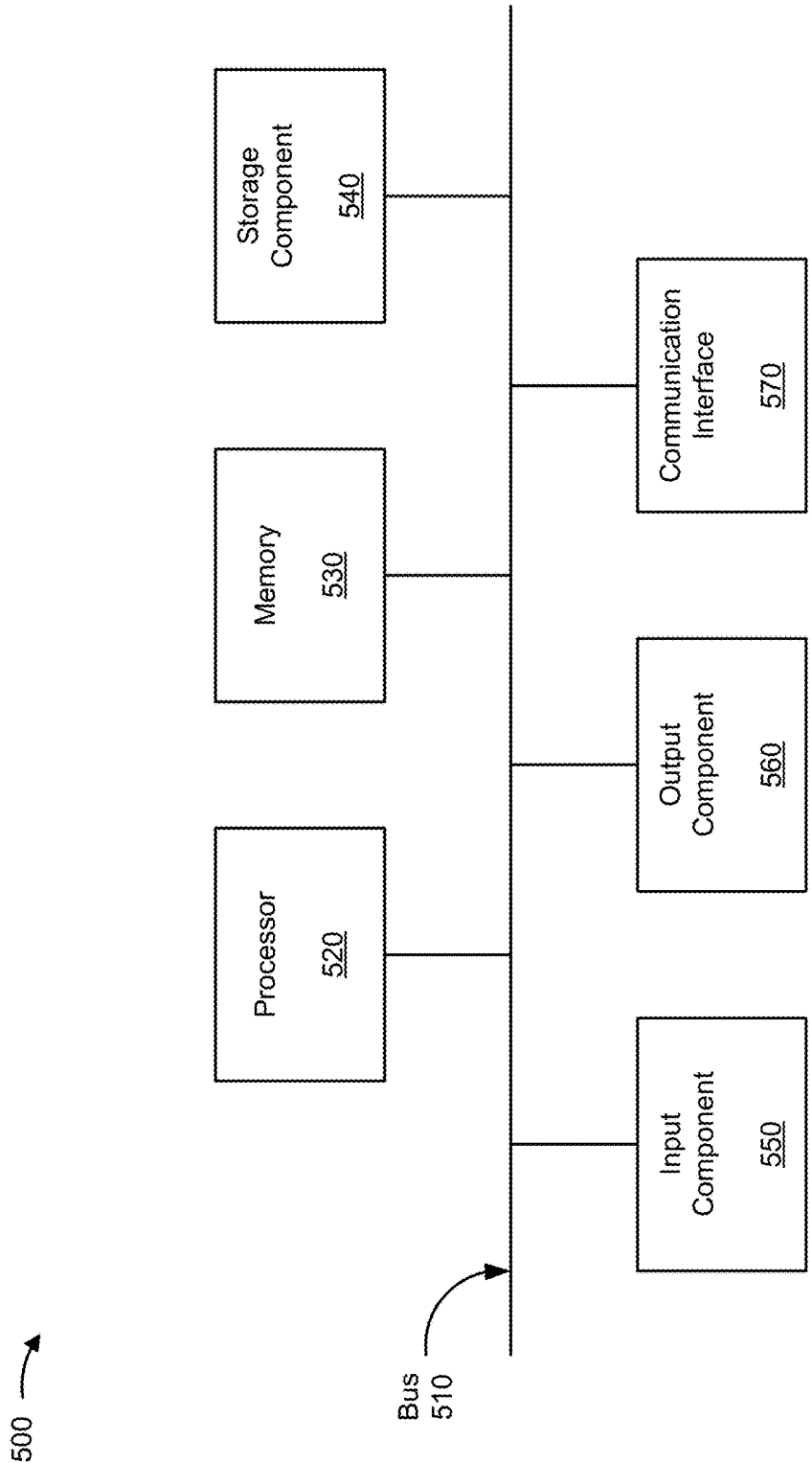
FIG. 5 is a diagram of example components of one or more devices of FIG. 4.

FIG. 5 is a diagram of example components of a device 500. Device 500 may correspond to client device 410, sensor 420, vitals monitoring platform 430, computing resource 434, and/or server device 440. In some implementations, client device 410, sensor 420, vitals monitoring platform 430, computing resource 434, and/or server device 440 may include one or more devices 500 and/or one or more components of device 500. As shown in FIG. 5, device 500 may include a bus 510, a processor 520, a memory 530, a storage component 540, an input component 550, an output component 560, and a communication interface 570.

Bus 510 includes a component that permits communication among the components of device 500. Processor 520 is implemented in hardware, firmware, or a combination of hardware and software. Processor 520 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 520 includes one or more processors capable of being programmed to perform a function. Memory 530 includes a random access memory (RAM), a read only memory (ROM), and/or another type of dynamic or static storage device (e.g., a flash memory, a magnetic memory, and/or an optical memory) that stores information and/or instructions for use by processor 520.

Storage component 540 stores information and/or software related to the operation and use of device 500. For example, storage component 540 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 550 includes a component that permits device 500 to receive information, such as via user input (e.g., a touch screen display, a keyboard, a keypad, a mouse, a button, a switch, and/or a microphone). Additionally, or alternatively, input component 550 may include a sensor for sensing information (e.g., a global positioning system (GPS) component, an accelerometer, a gyroscope, and/or an actuator). Output component 560 includes a component that provides output information from device 500 (e.g., a display, a speaker, and/or one or more light-emitting diodes (LEDs)).

Communication interface 570 includes a transceiver-like component (e.g., a transceiver and/or a separate receiver and transmitter) that enables device 500 to communicate with other devices, such as via a wired connection, a wireless connection, or a combination of wired and wireless connections. Communication interface 570 may permit device 500 to receive information from another device and/or provide information to another device. For example, communication interface 570 may include an Ethernet interface, an optical interface, a coaxial interface, an infrared interface, a radio frequency (RF) interface, a universal serial bus (USB) interface, a Wi-Fi interface, a cellular network interface, or the like.

Device 500 may perform one or more processes described herein. Device 500 may perform these processes based on processor 520 executing software instructions stored by a non-transitory computer-readable medium, such as memory 530 and/or storage component 540. A computer-readable medium is defined herein as a non-transitory memory device. A memory device includes memory space within a single physical storage device or memory space spread across multiple physical storage devices.

Software instructions may be read into memory 530 and/or storage component 540 from another computer-readable medium or from another device via communication interface 570. When executed, software instructions stored in memory 530 and/or storage component 540 may cause processor 520 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 5 are provided as an example. In practice, device 500 may include additional components, fewer components, different components, or differently arranged components than those shown in FIG. 5. Additionally, or alternatively, a set of components (e.g., one or more components) of device 500 may perform one or more functions described as being performed by another set of components of device 500.

Figure 6:
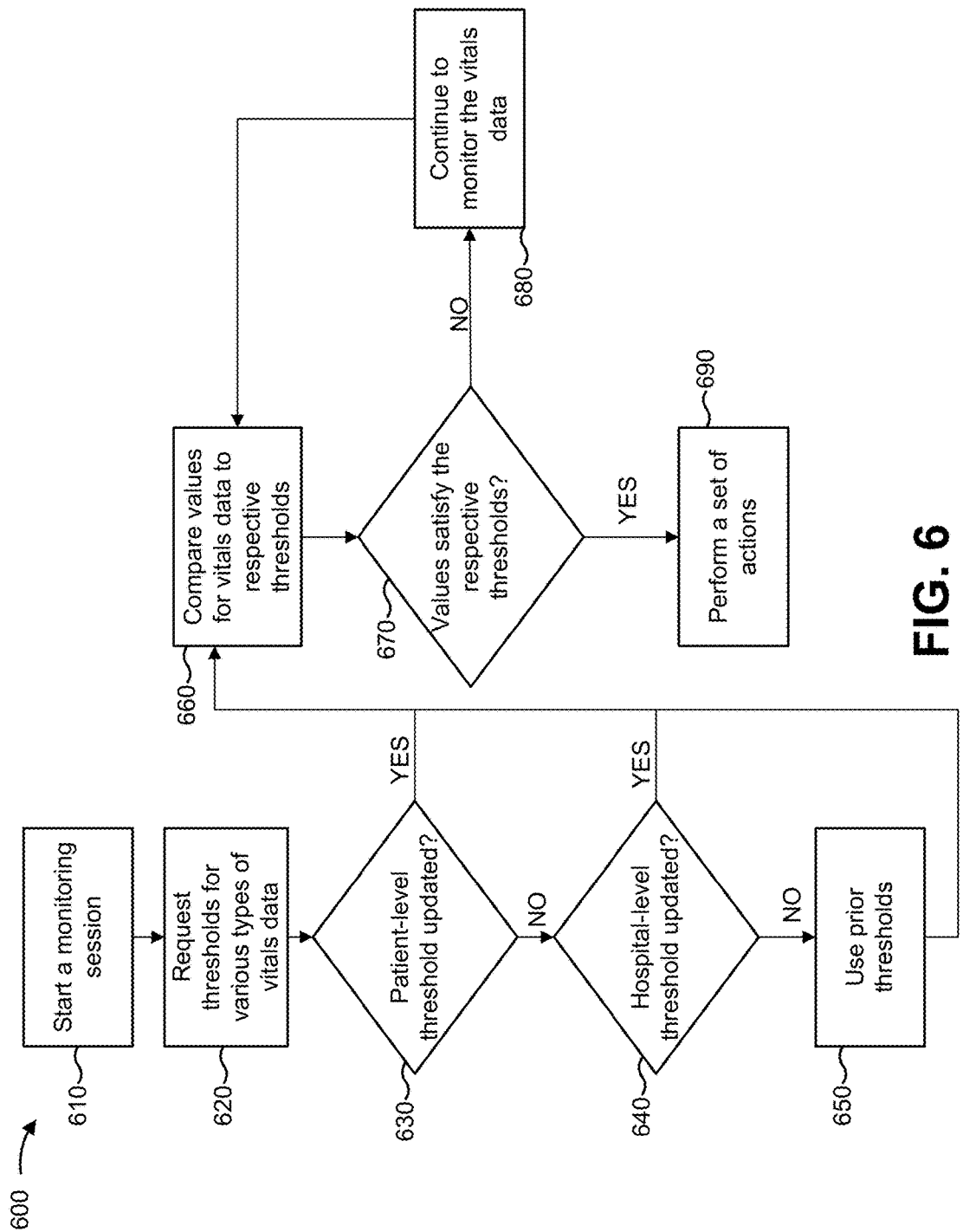
FIG. 6 is a flow chart of an example process for a vitals monitoring system.

FIG. 6 is a flow chart of an example process 600 for a vitals monitoring platform. In some implementations, one or more process blocks of FIG. 6 may be performed by vitals monitoring platform 430. In some implementations, one or more process blocks of FIG. 6 may be performed by another device or a group of devices separate from or including vitals monitoring platform 430, such as client device 410, sensor 420, or computing resource 434.

As shown in FIG. 6, process 600 may include starting a monitoring session (block 610). For example, vitals monitoring platform 430 (e.g., using computing resource 434, processor 520, output component 560, communication interface 570, and/or the like) may start a monitoring session for sensor 420. In some implementations, a monitoring session of sensor 420 may be associated with sensor 420 gathering vitals data from a patient (e.g., initiating gathering of vitals data, monitoring gathering of vitals data, modifying gathering of vitals data, and/or the like). In some implementations, vitals monitoring platform 430 may start a monitoring session by sending a set of instructions to sensor 420 (e.g., via client device 410). For example, vitals monitoring platform 430 may send a set of instructions to a local client device 410 in a hospital room associated with a patient with which sensor 420 is associated (e.g., via network 450) and the local client device 410 may provide the set of instructions to the appropriate sensor 420 based on information included in the set of instructions that identifies sensor 420 (e.g., via a Wi-Fi connection, a Bluetooth connection, a BLE connection, and/or the like).

In some implementations, vitals monitoring platform 430 may start the monitoring session based on receiving a set of instructions to start the monitoring session (e.g., based on input from client device 410). For example, vitals monitoring platform 430 may receive the set of instructions to start a monitoring session for a patient based on input from a remote client device 410 associated with a provider associated with providing healthcare services to the patient and/or based on input from a local client device 410 (e.g., located in a hospital room of the patient and used by an attending nurse). Additionally, or alternatively, vitals monitoring platform 430 may start the monitoring session based on a schedule (e.g., at a particular time of day, or minute of an hour), periodically, and/or the like.

Additionally, or alternatively, vitals monitoring platform 430 may start a monitoring session based on a result of processing historical vitals data for the patient. For example, vitals monitoring platform 430 may have generated a model based on a training set of data that includes various sets of vitals data and corresponding schedules for monitoring sessions. Continuing with the previous example, vitals monitoring platform 430 may use the model to process historical vitals data for a patient and may determine a schedule for monitoring sessions for the patient based on a result of processing the historical vitals data using the model. Continuing still with the previous example, vitals monitoring platform 430 may start the monitoring session according to the schedule that vitals monitoring platform 430 determined using the model. In some implementations, vitals monitoring platform 430 may update the model in real-time based on historical vitals data from other patients, so that vitals monitoring platform 430 can accurately determine a schedule for monitoring vitals data of the patient.

In this way, several different stages of the process for determining a schedule for monitoring vitals data are automated, which may remove human subjectivity and waste from the process, and which may improve speed and efficiency of the process and conserve computing resources (e.g., processor resources, memory resources, and/or the like). Furthermore, implementations described herein use a rigorous, computerized process to perform tasks or roles that were not previously performed or were previously performed using subjective human intuition or input. For example, currently there does not exist a technique to determine, in real-time (or near real-time), a schedule for monitoring vitals data based on vitals data for other patients. Further, automating this process conserves computing resources (e.g., processor resources, memory resources, and/or the like) that would otherwise be wasted in attempting to determine a schedule for monitoring vitals data, and computing resources of client device 410 that would be wasted monitoring vitals data at a higher rate than needed.

In this way, vitals monitoring platform 430 may start a monitoring session prior to requesting thresholds for various types of vitals data.

As further shown in FIG. 6, process 600 may include requesting thresholds for various types of vitals data (block 620). For example, vitals monitoring platform 430 (e.g., using computing resource 434, processor 520, output component 560, communication interface 570, and/or the like) may request, from server device 440, thresholds (e.g., information identifying a threshold, threshold data that identifies a baseline, and/or the like) for various types of vitals data (e.g., types of vitals data associated with the monitoring session). Continuing with the previous example, a patient may be associated with multiple sensors 420, however the monitoring session may be associated with a subset of the multiple sensors 420. In this case, vitals monitoring platform 430 request thresholds associated with the subset of the multiple sensors 420, rather than for all of the multiple sensors 420. This conserves computing resources of vitals monitoring platform 430 and/or server device 440 that would otherwise be consumed requesting and/or providing thresholds for sensors 420 not associated with the monitoring session. In this way, vitals monitoring platform 430 may request thresholds on a per-patient basis, a per-sensor 420 basis, and/or the like.

In some implementations, a threshold may include a default threshold (e.g., a hospital-level threshold) associated with a hospital, a rule, a regulation, an industry standard, and/or the like. Additionally, or alternatively, a threshold may include a customized threshold for a patient (e.g., a patient-level threshold). For example, a provider, such as a doctor, a nurse, and/or the like, may set a threshold for a particular patient, via input to client device 410, that is different from a default threshold. In some implementations, vitals monitoring platform 430 may determine a customized threshold for a patient using a model. For example, vitals monitoring platform 430 may have generated the model using a training set of data that includes historical vitals data for other patients and corresponding thresholds. Continuing with the previous example, vitals monitoring platform 430 may process historical vitals data of the patient using the model to determine a customized threshold for a patient. Additionally, or alternatively, and continuing with the previous example, vitals monitoring platform 430 may determine a default threshold for a hospital in a similar manner.

In some implementations, vitals monitoring platform 430 may receive information identifying the thresholds from server device 440 based on requesting the thresholds from server device 440. For example, server device 440 may provide information to vitals monitoring platform 430 that identifies a threshold associated with the monitoring session (e.g., a threshold for a particular sensor 420, for a particular patient, for a particular hospital, and/or the like) after identifying the requested thresholds (e.g., based on performing a lookup of information identifying a patient, a particular sensor 420, and/or the like associated with a monitoring session in a data structure to identify the requested thresholds).

In this way, vitals monitoring platform 430 may request thresholds for various types of vitals data prior to determining whether the thresholds have been updated.

As further shown in FIG. 6, process 600 may include determining whether a patient-level threshold has been updated (block 630). For example, vitals monitoring platform 430 (e.g., using computing resource 434, processor 520, memory 530, and/or the like) may determine whether a patient-level threshold has been updated (e.g., whether a customized threshold has been updated).

In some implementations, vitals monitoring platform 430 may perform a comparison of information identifying a current patient-level threshold (e.g., from server device 440) and information identifying a prior patient-level threshold (e.g., stored in memory 530) and may determine whether the patient-level threshold has been updated based on a result of performing the comparison. For example, vitals monitoring platform 430 may perform a lookup of the prior patient-level threshold in a data structure to perform the comparison. Additionally, or alternatively, server device 440 may provide information that indicates whether the patient-level data has been updated from a previously provided patient-level threshold (e.g., rather than providing information that identifies the current patient-level threshold when the patient-level threshold has not been updated) and vitals monitoring platform 430 may determine whether the patient-level threshold has been updated based on the information that identifies whether the patient-level threshold has been updated.

This conserves processing resources of vitals monitoring platform 430 when the patient-level threshold has not been updated by reducing or eliminating a need for vitals monitoring platform 430 to perform the comparison. Additionally, or alternatively, vitals monitoring platform 430 may determine whether a patient-level threshold is associated with a particular patient and/or sensor 420 based on information from server device 440. For example, a particular patient and/or sensor 420 may not be associated with a patient-level threshold (e.g., a doctor, a nurse, and/or the like may not have set a customized threshold for the particular patient).

In this way, vitals monitoring platform 430 may determine whether a patient-level threshold has been updated prior to determining whether a hospital-level threshold has been updated.

As further shown in FIG. 6, if the vitals monitoring platform determines that the patient-level threshold has not been updated (block 630—NO), then process 600 may include determining whether a hospital-level threshold has been updated (block 640). For example, if vitals monitoring platform 430 determines that the patient-level threshold has not been updated (or that a patient-level threshold has not been configured for a patient), then vitals monitoring platform 430 (e.g., using computing resource 434, processor 520, memory 530, and/or the like) may determine whether a hospital-level threshold has been updated. In some implementations, vitals monitoring platform 430 may determine whether a hospital-level threshold has been updated in a manner that is similar to that described above with regard to block 630. In this way, vitals monitoring platform 430 may determine whether a hospital-level threshold has been updated prior to using a threshold to analyze vitals data.

As further shown in FIG. 6, if the vitals monitoring platform determines that the hospital-level threshold has not been updated (block 640—NO), then process 600 may include determining to use prior thresholds (block 650). For example, if vitals monitoring platform 430 determines that the hospital-level threshold has not been updated (and/or that the patient-level threshold has not been updated or set), then vitals monitoring platform 430 (e.g., using computing resource 434, processor 520, memory 530, and/or the like) may determine to use prior thresholds.

In some implementations, vitals monitoring platform 430 may determine to use a prior hospital-level threshold if a hospital-level threshold has not been updated. Additionally, or alternatively, vitals monitoring platform 430 may determine to use a hospital-level threshold if a patient-level threshold has not been set for a particular patient. Additionally, or alternatively, vitals monitoring platform 430 may determine to use a prior patient-level threshold if a patient-level threshold has not been updated.

In this way, vitals monitoring platform 430 may determine to use prior thresholds prior to comparing values for vitals data to respective thresholds.

As further shown in FIG. 6, process 600 may include comparing values for vitals data to respective thresholds (block 660). For example, vitals monitoring platform 430 (e.g., using computing resource 434, processor 520, and/or the like) may compare values for vitals data to respective thresholds. Continuing with the previous example, vitals monitoring platform 430 may compare a first value for a first type of vitals data to a first threshold, may compare a second value for a second type of vitals data to a second threshold, and so forth.

In some implementations, if the patient-level threshold has been updated (block 630—YES), then vitals monitoring platform 430 may compare values for vitals data to the updated patient-level threshold. Additionally, or alternatively, if the hospital-level threshold has been updated (block 640—YES), then vitals monitoring platform 430 may compare values for vitals data to an updated hospital-level threshold. Additionally, or alternatively, vitals monitoring platform 430 may compare values for vitals data to a prior patient-level threshold, a prior hospital-level threshold, and/or the like (e.g., based on the patient-level threshold not being updated, based on a patient-level threshold not being set for a patient, and/or based on the hospital-level threshold not being updated).

In some implementations, rather than comparing values for vitals data to respective thresholds, vitals monitoring platform 430 may process the values using a model (e.g., to determine whether particular combinations of values, associated with health-related issues, are present in the vitals data). For example, vitals monitoring platform 430 may have generated the model based on a training set of data that includes various combinations of values for vitals data and information identifying corresponding health-related issues. Additionally, or alternatively, vitals monitoring platform 430 may process values for the vitals data to determine whether the values include a trend, a pattern, and/or the like (e.g., that indicates a health-related issue for a patient). In some implementations, vitals monitoring platform 430 may determine a score for a patient, for a type of vitals data, and/or the like (e.g., a score that indicates a health-related issue, that indicates satisfaction of a threshold, and/or the like). For example, vitals monitoring platform 430 may determine a score based on values for vitals data satisfying a threshold, based on the vitals data including a particular combination of values, a particular trend of values, a particular pattern of values, and/or the like.

In this way, vitals monitoring platform 430 can use the model to identify (or predict) health-related issues that are indicated by complex combinations of values, complex trends and/or patterns in values for vitals data, and/or the like. For example, vitals monitoring platform 430 can use the model to identify health-related issues that cannot otherwise be identified by a human actor and/or manual processing of vitals data.

In this way, vitals monitoring platform 430 may compare values for vitals data to respective thresholds prior to determining whether the values satisfy the respective thresholds.

As further shown in FIG. 6, process 600 may include determining whether the values satisfy the respective thresholds (block 670). For example, vitals monitoring platform 430 (e.g., using computing resource 434, processor 520, and/or the like) may determine whether the values satisfy the respective thresholds.

In some implementations, vitals monitoring platform 430 may determine whether the values satisfy the respective thresholds in real-time (or near real-time), as vitals data is streamed to vitals monitoring platform 430, based on a result of comparing the values for the vitals data to the respective thresholds, and/or the like. Additionally, or alternatively, vitals monitoring platform 430 may determine whether the values includes a particular combination of values, a combination of values relative to respective thresholds, and/or the like. For example, vitals monitoring platform 430 may perform this determination based on a result of processing the values using a model, in real-time (or near real-time), as vitals data is streamed to vitals monitoring platform 430, and/or the like. Additionally, or alternatively, vitals monitoring platform 430 may determine whether values for vitals data includes a pattern, a trend, and/or the like (e.g., as vitals data is streamed to vitals monitoring platform 430, based on a result of processing vitals data using a model, etc.). In this way, vitals monitoring platform 430 may identify a health-related issue based on a threshold, when the health-related issue cannot be identified using a threshold, and/or the like.

In this way, vitals monitoring platform 430 may determine whether the values satisfy the respective thresholds prior to performing various actions.

As further shown in FIG. 6, if the vitals monitoring platform determines that the values do not satisfy the respective thresholds (block 670—NO), then process 600 may include continuing to monitor the vitals data (block 680). For example, vitals monitoring platform 430 (e.g., using computing resource 434, processor 520, input component 550, communication interface 570, and/or the like) may continue to monitor the vitals data. In some implementations, vitals monitoring platform 430 may continue to receive vitals data from sensor 420 (e.g., via client device 410). Additionally, or alternatively, vitals monitoring platform 430 may continue to compare values for the vitals data to the respective thresholds and to determine whether the values satisfy the respective thresholds. In other words, process 600 may include returning to block 660.

As further shown in FIG. 6, if the vitals monitoring platform determines that the values satisfy the respective thresholds (block 670—YES), then process 600 may include performing a set of actions (block 690). For example, vitals monitoring platform 430 (e.g., using computing resource 434, processor 520, output component 560, communication interface 570, and/or the like) may perform a set of actions.

In some implementations, vitals monitoring platform 430 may perform analytics on the vitals data. Additionally, or alternatively, vitals monitoring platform 430 may generate a graphical output (e.g., for the vitals data). In some implementations, vitals monitoring platform 430 may generate a graphical output and/or may configure a user interface based on a user profile associated with client device 410 (e.g., logged into vitals monitoring platform 430). For example, vitals monitoring platform 430 may provide patient-level data to a healthcare provider via a user interface, but may provide aggregated and anonymized patient-related data to a manager of a hospital. In some implementations, vitals monitoring platform 430 may provide information via a user interface in a continuous and live manner (e.g., as the information, such as vitals data, a result of analyzing vitals data, and/or the like, is received by vitals monitoring platform 430, is determined by vitals monitoring platform 430, as the information changes, and/or the like). Additionally, or alternatively, vitals monitoring platform 430 may trigger an alarm, send a message (e.g., may selectively generate and/or send an alert based on vitals data associated with a patient, based on a result of analyzing the vitals data, and/or the like), schedule a meeting, and/or the like in a manner similar to that described elsewhere herein.

Additionally, or alternatively, vitals monitoring platform 430 may perform revenue tracking-related actions. For example, vitals monitoring platform 430 may monitor costs related to provider time spent remotely providing healthcare services to a patient, revenue generated from use of sensor 420 (e.g., a test related to sensor 420), and/or the like and may output this information via a user interface associated with client device 410.

Additionally, or alternatively, vitals monitoring platform 430 may provide a set of instructions to client device 410 and/or sensor 420 in a manner similar to that described elsewhere herein. Additionally, or alternatively, vitals monitoring platform 430 may activate a camera and/or a microphone on client device 410 for an audio and/or video conferencing session. Additionally, or alternatively, vitals monitoring platform 430 may facilitate an audio and/or video conferencing session by establishing a P2P communication session between a local client device 410 and a remote client device 410, similar to that described elsewhere herein.

Additionally, or alternatively, vitals monitoring platform 430 may trigger administration of medicine to a patient (e.g., based on vitals data). For example, vitals monitoring platform 430 may cause a medicine dispenser to begin administration of a particular medicine, to adjust an amount of a particular medicine administered to a patient, and/or to stop administration of a particular medicine. Additionally, or alternatively, and as another example, vitals monitoring platform 430 may send a message to client device 410 associated with a healthcare provider to notify the healthcare provider to administer medicine (or adjust administration of the medicine) to a patient. Additionally, or alternatively, vitals monitoring platform 430 may detect addition or removal of a particular sensor 420 from a set of sensors 420 (e.g., based on a local client device 410 detecting or not detecting a wireless signal from sensor 420).

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

In this way, vitals monitoring platform 430 may facilitate and/or manage remote provisioning of healthcare to a patient. This reduces or eliminates inefficiencies that would otherwise be present with non-remote provisioning of healthcare services. In addition, this conserves processing resources that would otherwise be consumed via an inefficient manual use of a device to provide healthcare services to a patient by providing a tool that can be used to reduce or eliminate a need for a human actor. Further, this improves an accuracy of providing healthcare services to a patient, thereby improving provisioning of the healthcare services.

The foregoing disclosure provides illustration and description, but is not intended to be exhaustive or to limit the implementations to the precise form disclosed. Modifications and variations are possible in light of the above disclosure or may be acquired from practice of the implementations.

Although some implementations were described in the context of a healthcare provider providing healthcare services to a patient, the implementations apply equally to other contexts, such as another type of responsible party monitoring vitals data and/or environmental data for an operator of a vehicle, an individual that works with chemicals, and/or the like.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A system, comprising:
a platform that includes one or more memory devices and one or more processors communicatively coupled to the one or more memory devices,
wherein the platform is to connect and communicate bi-directionally with a plurality of devices via a gateway device,
the gateway device being a user device associated with a patient,
the user device and the at least some of the plurality of devices being located in a same physical location,
wherein the plurality of devices includes different types of devices and devices manufactured by a plurality of different third parties,
wherein at least some of the plurality of devices include sensors capable of gathering vitals data from the patient,
wherein the vitals data includes a plurality of different types of vitals data,
wherein the platform is to support continuous and live streaming of the vitals data from the sensors,
wherein the platform is to:
receive threshold data on a per patient basis,
wherein the threshold data identifies a baseline for one or more of the plurality of different types of vitals data,
selectively generate an alert based on the vitals data and the threshold data, and
provide the alert to a responsible party when the alert is generated.

2. The system of claim 1, wherein the same physical location is a building or a room.

3. The system of claim 1, wherein the platform is further to:
facilitate remote control of the sensors by a remote device located in a different location than the gateway device and the at least some of the plurality of devices that include the sensors.

4. The system of claim 1, wherein the vitals data includes at least two of:
heart rate data of the patient,
respiratory rate data of the patient,
body temperature data of the patient,
oxygen saturation data of the patient,
blood pressure data of the patient, or
electrocardiography data of the patient.

5. The system of claim 1, wherein the at least some of the plurality of devices are wearable devices associated with the patient.

6. The system of claim 1, wherein the platform is further to:
perform an analysis of a trend or a pattern in the vitals data prior to selectively generating the alert,
wherein the alert is associated a result of performing the analysis of the trend or the pattern.

7. The system of claim 1, wherein the platform is further to:
perform an analysis of a combination of values included in the vitals data prior to selectively generating the alert,
wherein the alert is associated with a result of performing the analysis of the combination of the values.

8. A patient monitoring system, comprising:
a platform that includes one or more memory devices and one or more processors communicatively coupled to the one or more memory devices,
wherein the platform is to connect and communicate bi-directionally with a plurality of devices via a gateway device,
the gateway device being a user device associated with a patient,
the user device and the at least some of the plurality of devices being located in a same physical location,
wherein at least some of the plurality of devices are wearable devices that include sensors capable of gathering vitals data from a patient,
wherein the at least some of the plurality of devices are located in a same location as the gateway device,
wherein the platform is to support continuous and live streaming of the vitals data from the sensors,
wherein the platform is to:
perform an analysis of the vitals data on a per patient basis,
selectively generate an alert based on a result of performing the analysis, and
provide the alert to a responsible party when the alert is generated.

9. The patient monitoring system of claim 8, wherein the platform is further to:
facilitate audio conferencing or video conferencing between the gateway device and a remote device that is located in a different location than the gateway device and the at least some of the plurality of devices that include the sensors.

10. The patient monitoring system of claim 8, wherein the platform is further to:
schedule a meeting with the responsible party based on the result of performing the analysis.

11. The patient monitoring system of claim 8, wherein the platform is further to:
provide a set of instructions to the at least some of the plurality of devices via the gateway device to modify operations of the sensors.

12. The patient monitoring system of claim 8, wherein the sensors include:
a first sensor to gather heart rate data from the patient,
a second sensor to gather respiratory rate data from the patient, a third sensor to gather body temperature data from the patient, a fourth sensor to gather oxygen saturation data from the patient, a fifth sensor to gather blood pressure data of the patient, or a sixth sensor to gather electrocardiography data of the patient.

13. The patient monitoring system of claim 8, wherein the platform is further to:

perform continuous and live updates of a user interface based on the continuous and live streaming of the vitals data, wherein the user interface is associated with providing the vitals data for display.

14. The patient monitoring system of claim 8, wherein the platform is further to:

connect and communicate bi-directionally with another plurality of devices that are remote to the at least some of the plurality of devices.

15. A remote care system, comprising:

a platform that includes one or more memory devices and one or more processors communicatively coupled to the one or more memory devices, wherein the platform is to connect and communicate bi-directionally with a plurality of devices via a gateway device, the gateway device being a user device associated with a patient, the user device and the at least some of the plurality of devices being located in a same physical location, wherein at least some of the plurality of devices include sensors capable of gathering vitals data from a patient, wherein the vitals data includes a plurality of different types of vitals data, wherein the platform is to connect and communicate bi-directionally with another plurality of devices, wherein the other plurality of devices are remote to the gateway device and the at least some of the plurality of devices, wherein the platform is to support continuous and live streaming of the vitals data from the sensors, wherein the platform is to perform a set of actions on a per patient basis based on analyzing the vitals data.

16. The remote care system of claim 15, wherein the set of actions includes:

causing the sensors to increase a rate of monitoring the vitals data.

17. The remote care system of claim 15, wherein the set of actions includes:

causing the sensors to decrease a rate of monitoring the vitals data.

18. The remote care system of claim 15, wherein the set of actions includes:

providing a set of instructions from a remote device, of the other plurality of devices, to the at least some of the plurality of devices to modify operations of the sensors.

19. The remote care system of claim 15, wherein the set of actions includes:

performing an analysis of the vitals data on the per patient basis, selectively generating an alert based on a result of performing the analysis, and providing the alert to a responsible party when the alert is generated.

20. The remote care system of claim 15, wherein the plurality of devices includes different types of devices and devices manufactured by a plurality of different third parties.

* * * * *